US009204789B2

(12) United States Patent
Wenchell et al.

(10) Patent No.: US 9,204,789 B2
(45) Date of Patent: Dec. 8, 2015

(54) ASYMMETRICAL ANOSCOPE

(75) Inventors: Thomas Wenchell, Durham, CT (US);
Christopher Switalski, Suffield, CT (US)

(73) Assignee: Covidien LP, Mansfield, MA (US)

( * ) Notice: Subject to any disclaimer, the term of this patent is extended or adjusted under 35 U.S.C. 154(b) by 303 days.

(21) Appl. No.: 12/880,215

(22) Filed: Sep. 13, 2010

(65) Prior Publication Data

US 2011/0087075 A1    Apr. 14, 2011

Related U.S. Application Data

(60) Provisional application No. 61/249,652, filed on Oct. 8, 2009.

(51) Int. Cl.
| | | |
|---|---|---|
| *A61B 1/32* | (2006.01) | |
| *A61B 1/00* | (2006.01) | |
| *A61B 1/31* | (2006.01) | |
| *A61B 17/00* | (2006.01) | |
| *A61B 17/34* | (2006.01) | |

(52) U.S. Cl.
CPC ............... *A61B 1/32* (2013.01); *A61B 1/00154* (2013.01); *A61B 1/31* (2013.01); *A61B 2017/0042* (2013.01); *A61B 2017/00438* (2013.01); *A61B 2017/3452* (2013.01)

(58) Field of Classification Search
USPC .................................. 600/201, 203, 235, 220
See application file for complete search history.

(56) References Cited

U.S. PATENT DOCUMENTS

| | | | | |
|---|---|---|---|---|
| 267,906 | A | * | 11/1882 | Law ............................. 600/184 |
| 295,798 | A | | 3/1884 | Pagett |
| 314,132 | A | | 3/1885 | Ingersoll |
| 357,216 | A | | 2/1887 | McCall |
| 457,787 | A | | 8/1891 | Leisenring |
| 2,290,571 | A | | 7/1942 | Peyton |
| 2,469,880 | A | | 5/1949 | Kowan |
| 2,754,822 | A | | 7/1956 | Emelock |
| 2,769,441 | A | | 11/1956 | Abramson |
| 2,922,415 | A | | 1/1960 | Campagna |
| 3,051,176 | A | | 8/1962 | Alberti |
| 3,132,645 | A | | 5/1964 | Gasper |
| 3,459,175 | A | | 8/1969 | Miller |
| 3,701,347 | A | | 10/1972 | Belkin |

(Continued)

FOREIGN PATENT DOCUMENTS

| | | |
|---|---|---|
| DE | 3717607 | 12/1988 |
| EP | 1929959 | 6/2008 |

(Continued)

OTHER PUBLICATIONS www.thefreedictionary.com/circumference, definition of "circumference", accessed Mar. 13, 2014.*

(Continued)

*Primary Examiner* — Jan Christopher Merene

(57) ABSTRACT

An insertion device for use during surgical procedure to enlarge an opening in a patient's tissue to facilitate access to an internal treatment site with a surgical instrument. The insertion device includes an anoscope including a flange, and an elongate body having proximal and distal ends extending distally from the flange along a longitudinal axis. The anoscope may include a configuration that is asymmetrical about a plane extending along the longitudinal axis that bisects the flange.

22 Claims, 11 Drawing Sheets

(56) References Cited

U.S. PATENT DOCUMENTS

| | | | |
|---|---|---|---|
| 4,220,155 A | 9/1980 | Kimberling et al. | |
| 4,341,211 A | 7/1982 | Kline | |
| 4,834,067 A | 5/1989 | Block | |
| 4,957,499 A | 9/1990 | Lipatov et al. | |
| 5,122,149 A | 6/1992 | Broome | |
| 5,176,127 A | 1/1993 | Dormia | |
| 5,256,149 A | 10/1993 | Banik et al. | |
| 5,351,674 A | 10/1994 | Hawks | |
| D353,197 S | 12/1994 | Hawks | |
| 5,404,870 A | 4/1995 | Brinkerhoff et al. | |
| 5,425,736 A | 6/1995 | Wadsworth | |
| D360,261 S | 7/1995 | Swanson et al. | |
| 5,464,412 A | 11/1995 | Budding | |
| 5,503,109 A * | 4/1996 | Sporn | 119/633 |
| 5,509,893 A | 4/1996 | Pracas | |
| D384,412 S | 9/1997 | Mainiero | |
| 5,716,329 A | 2/1998 | Dieter | |
| 5,741,273 A | 4/1998 | O'Regan | |
| 5,916,150 A | 6/1999 | Sillman | |
| 5,931,776 A | 8/1999 | Dotolo | |
| 5,957,902 A | 9/1999 | Teves | |
| 6,083,241 A | 7/2000 | Longo et al. | |
| 6,102,271 A | 8/2000 | Longo et al. | |
| 6,126,594 A | 10/2000 | Bayer | |
| 6,136,009 A | 10/2000 | Mears | |
| 6,142,933 A | 11/2000 | Longo | |
| 6,152,936 A | 11/2000 | Christy et al. | |
| 6,315,713 B1 | 11/2001 | Takada | |
| 6,364,852 B1 | 4/2002 | Lee | |
| 6,428,473 B1 | 8/2002 | Leonard et al. | |
| 6,497,654 B1 | 12/2002 | Leonard et al. | |
| 6,503,192 B1 | 1/2003 | Ouchi | |
| 6,503,912 B1 | 1/2003 | Wagner et al. | |
| 6,506,157 B1 | 1/2003 | Teigman et al. | |
| 6,547,798 B1 | 4/2003 | Yoon et al. | |
| 6,616,603 B1 | 9/2003 | Fontana | |
| 6,702,741 B2 | 3/2004 | Rioux et al. | |
| 6,740,098 B2 | 5/2004 | Abrams et al. | |
| 6,740,101 B2 | 5/2004 | Houser et al. | |
| 6,761,687 B1 | 7/2004 | Doshi et al. | |
| 7,029,438 B2 | 4/2006 | Morin et al. | |
| 7,037,314 B2 | 5/2006 | Armstrong | |
| D564,657 S | 3/2008 | Tsai | |
| 7,452,329 B2 | 11/2008 | Bastia et al. | |
| 7,611,458 B2 | 11/2009 | Sias | |
| 8,231,042 B2 * | 7/2012 | Hessler et al. | 227/179.1 |
| 8,337,401 B2 * | 12/2012 | Rebuffat et al. | 600/184 |
| 2002/0170184 A1 * | 11/2002 | Lothe | 30/295 |
| 2003/0069472 A1 | 4/2003 | Butler | |
| 2003/0130559 A1 | 7/2003 | Morin et al. | |
| 2004/0260152 A1 | 12/2004 | Sant et al. | |
| 2005/0234299 A1 * | 10/2005 | Eitenmuller et al. | 600/160 |
| 2005/0277811 A1 | 12/2005 | Richards et al. | |
| 2006/0009797 A1 | 1/2006 | Armstrong | |
| 2006/0036129 A1 | 2/2006 | Sias | |
| 2006/0155169 A1 * | 7/2006 | Bastia et al. | 600/199 |
| 2006/0212046 A1 | 9/2006 | Pearce et al. | |
| 2007/0043264 A1 | 2/2007 | Gillis et al. | |
| 2008/0091218 A1 | 4/2008 | Richardson | |
| 2008/0097478 A1 | 4/2008 | Doughty et al. | |
| 2008/0262511 A1 | 10/2008 | Delaney | |
| 2008/0275306 A1 | 11/2008 | Rebuffat et al. | |
| 2009/0005647 A1 | 1/2009 | Bozdag | |
| 2009/0012356 A1 | 1/2009 | Dann et al. | |
| 2009/0192352 A1 | 7/2009 | Regadas | |
| 2009/0203961 A1 | 8/2009 | Regadas | |
| 2009/0259110 A1 * | 10/2009 | Bastia et al. | 600/235 |
| 2009/0306481 A1 * | 12/2009 | Bastia | 600/249 |
| 2010/0145148 A1 | 6/2010 | Wenchell | |
| 2010/0280523 A1 * | 11/2010 | Chen et al. | 606/110 |

FOREIGN PATENT DOCUMENTS

| | | | | |
|---|---|---|---|---|
| WO | WO 2007049308 A1 * | 5/2007 | | |
| WO | WO 2007094016 A1 * | 8/2007 | | A61B 1/31 |
| WO | 2009/092194 | 7/2009 | | |

OTHER PUBLICATIONS

PCT International Search Report for PCT/IT2005/000619 filed on Oct. 26, 2005 in the name of Carlo Rebuffat, et al.

* cited by examiner

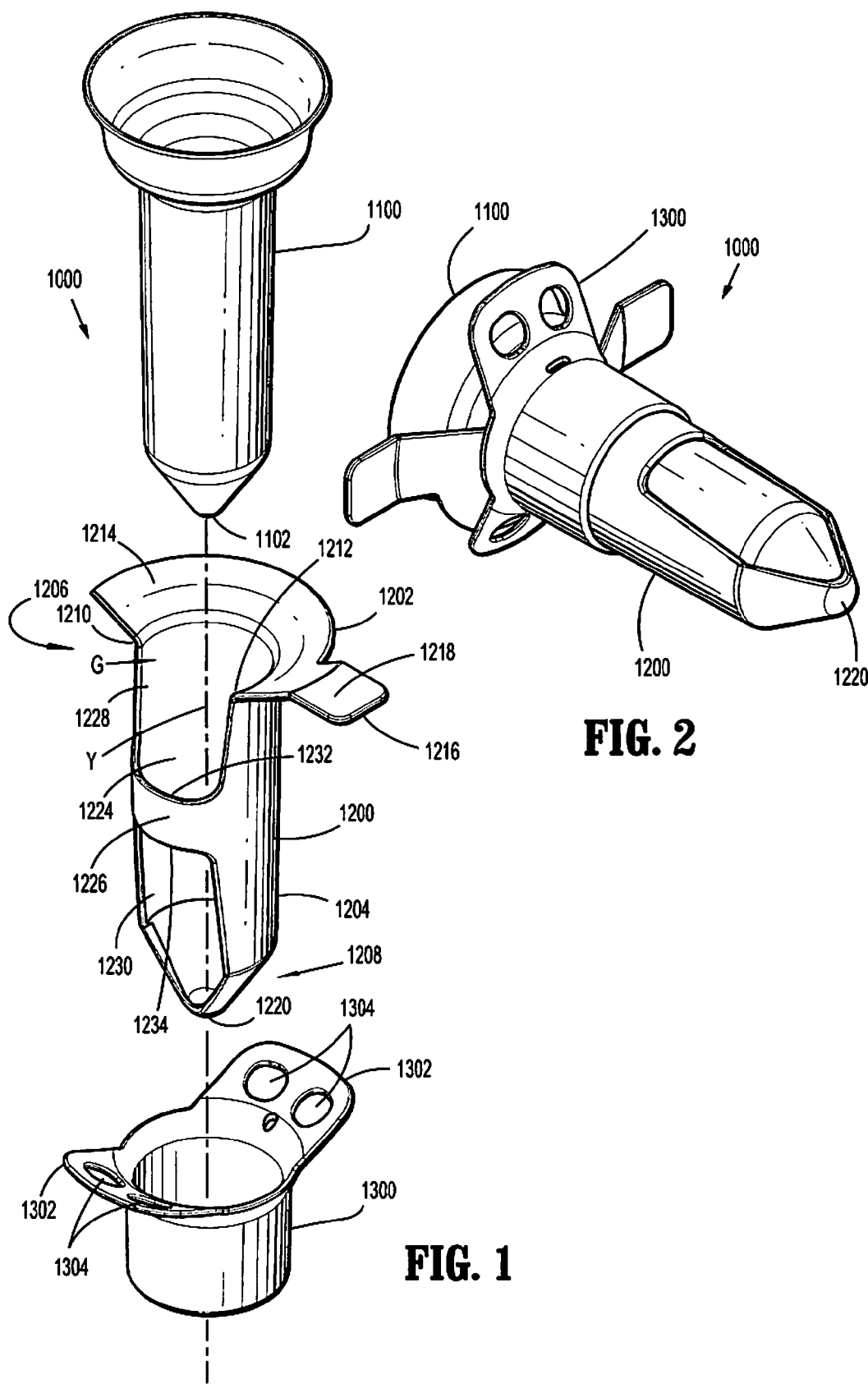

ASYMMETRICAL ANOSCOPE

This application claims priority from provisional application Ser. No. 61/249,652, filed Oct. 8, 2009, the entire contents of which are incorporated herein by reference.

BACKGROUND

1. Technical Field

The present disclosure relates to an insertion device that is adapted for positioning within an opening in tissue to facilitate access to an internal treatment site with a surgical instrument. More particularly, the present disclosure relates to an anoscope kit for use with a surgical fastener applying apparatus.

2. Background of Related Art

A medical device used in the dilation and/or inspection of an internal treatment site, e.g., a treatment site within a patient's anus, rectum, and/or colon, is often referred to as an anoscope. Anoscopes generally comprise a hollow body that is configured and dimensioned for insertion into an opening in the patient's tissue; either an opening that is natural and pre-existing, e.g., the patient's anus, or an opening that is formed by a clinician, e.g., an incision. The hollow body of the anoscope will generally include structure that is configured and dimensioned to dilate, and cover, the opening in the patient's tissue, as well as structure at the distal end thereof that is configured and dimensioned to accommodate the target tissue, e.g., hemorrhoidal tissue, such as a gap, notch, or slot.

After positioning the anoscope within the opening in the patient's tissue, the interior of the hollow body provides a passage through which the clinician can inspect the internal treatment site, and perform the surgical procedure. For example, anoscopes are particularly useful in the inspection and treatment of hemorrhoidal tissue, as well as tissue positioned adjacent thereto, e.g., mucosal tissue, during hemorrhoid procedures. During these procedures, the clinician will usually excise the target tissue, and thereafter suture the treated area.

An anoscope including structure that is configured and dimensioned to increase maneuverability and manipulation of the anoscope would be desirable in the interests of allowing a clinician to more easily access the tissue that is the subject of the surgical procedure.

SUMMARY

In one aspect of the present disclosure, an insertion device is disclosed for use during a surgical procedure to enlarge an opening in a patient's tissue to facilitate access to an internal treatment site with a surgical instrument. The disclosed insertion device includes an anoscope with a flange, and an elongate body having proximal and distal ends that extends distally from the flange along a longitudinal axis. In one embodiment, the anoscope includes a configuration that is asymmetrical about a plane extending along the longitudinal axis that bisects the flange.

It is envisioned that the body of the anoscope may include a first opening spaced longitudinally from a second opening, wherein the first and second openings are aligned along the longitudinal axis.

The flange can include first and second circumferentially spaced ends defining a gap therebetween that is configured and dimensioned to receive tissue. In one embodiment, the anoscope includes at least one wing that extends outwardly from the flange relative to the longitudinal axis. For example, the anoscope may include a single wing positioned either adjacent one of the ends of the flange, or alternatively, between the ends of the flange. In another embodiment, rather than just a single wing, the anoscope may include a first wing and a second wing. In this embodiment, it is envisioned that the first wing may extend outwardly from the flange a first distance, whereas the second wing may extend outwardly from the flange a second, greater distance. To enhance maneuverability of the anoscope, the wing(s) may include a lip extending along a periphery creating a surface adjacent the lip to facilitate maneuverability.

The presently disclosed insertion device may also include a dilator that is configured and dimensioned for positioning within the body of the anoscope.

The insertion device may include a port defining a longitudinal opening therethrough that is configured and dimensioned to receive the anoscope, wherein the port itself is configured and dimensioned for positioning within the opening in the tissue. It is envisioned that the port may include a pair of wings extending outwardly therefrom along an axis that is transverse in relation to the longitudinal axis such that the longitudinal axis and the transverse axis define an acute angle therebetween. For example, the angle defined between the longitudinal axis and the transverse axis may be approximately equal to 55°.

The present disclosure also provides in another aspect, an insertion device that includes an anoscope with a flange, and an elongate body having proximal and distal ends that extends distally from the flange along a longitudinal axis. The anoscope includes a configuration that is symmetrical about a plane extending along the longitudinal axis that bisects the flange. The anoscope includes a pair of wings that extend outwardly from the flange relative to the longitudinal axis and curve outwardly away from the distal end, wherein each of the wings includes a lip extending in a proximal direction that is positioned along a peripheral edge thereof.

The distal end of the anoscope preferably includes a closed distal tip that is configured and dimensioned to facilitate atraumatic advancement and/or rotation of the anoscope.

In yet another aspect of the present disclosure, an insertion device is disclosed including a port defining a longitudinal opening therethrough that is configured and dimensioned for positioning within the opening in the tissue, an anoscope that is configured and dimensioned for positioning within the longitudinal opening of the port, and a dilator that is configured and dimensioned for positioning within the body of the anoscope. The anoscope includes a flange, and an elongate body extending distally from the flange along a longitudinal axis. The anoscope has a configuration that is asymmetrical about a plane extending along the longitudinal axis that bisects the flange.

It is envisioned that the anoscope may also include at least one wing extending outwardly from the flange relative to the longitudinal axis.

The port of the insertion device may include a pair of wings that extend outwardly therefrom, wherein at least one of the wings includes an aperture that is configured and dimensioned to receive a flexible member such as a suture to facilitate attachment of the port to the patient's tissue. It is envisioned that the wings may extend outwardly along an axis that is transverse in relation to the longitudinal axis such that the longitudinal axis and the transverse axis define an acute angle therebetween.

These and other features of the presently disclosed insertion device will become more readily apparent to those skilled in the art through reference to the detailed description of various embodiments of the present disclosure that follows.

BRIEF DESCRIPTION OF THE DRAWINGS

Various embodiments of the present disclosure are described herein below with reference to the drawings, wherein:

FIG. 1 is a front, perspective view of an insertion device including an obturator, an anoscope, and a port in accordance with one embodiment of the present disclosure;

FIG. 2 is a side, perspective view of the insertion device of FIG. 1 upon assembly;

DETAILED DESCRIPTION

Figure 3:
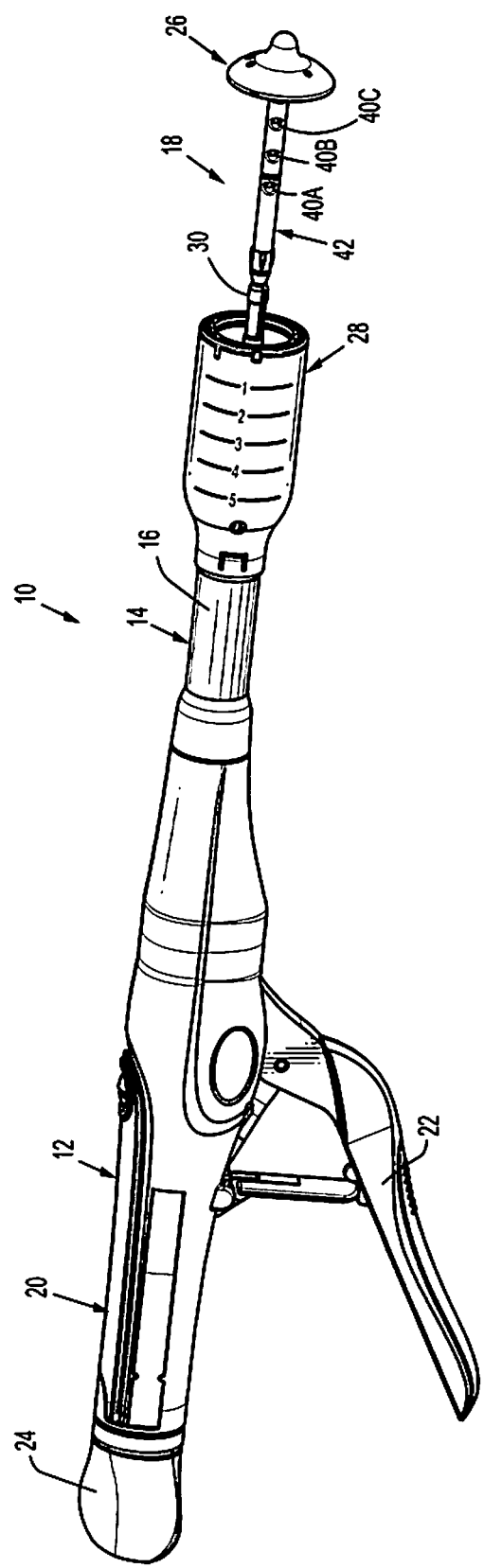
FIG. 3 is a side, perspective view of a surgical fastener applying apparatus for use with the presently disclosed insertion device during a surgical procedure.

The presently disclosed insertion device will now be described in detail with reference to the drawings, wherein like reference numerals designate identical or corresponding elements. Throughout the following description, the term "proximal" should be understood as referring to the portion of the insertion device, or component thereof, that is closer to the clinician during proper use, and the term "distal" should be understood as referring to the portion of the insertion device, or component thereof, that is further from the clinician during proper use. Additionally, the terms "hemorrhoidal tissue," and the like, should be understood as referring to hemorrhoidal tissue, as well as tissue positioned adjacent to hemorrhoidal tissue, including mucosal tissue. While the presently disclosed insertion device is particularly suited for surgical hemorrhoid procedures, the term "hemorrhoid procedure" should be understood to encompass surgical hemorrhoidectomies, hemorrhoidopexies, mucosectomies, procedures for the treatment of colon prolapse, and all such related procedures. The present disclosed insertion device can also be used for surgical procedures other than hemorrhoid procedures.

Figure 13:
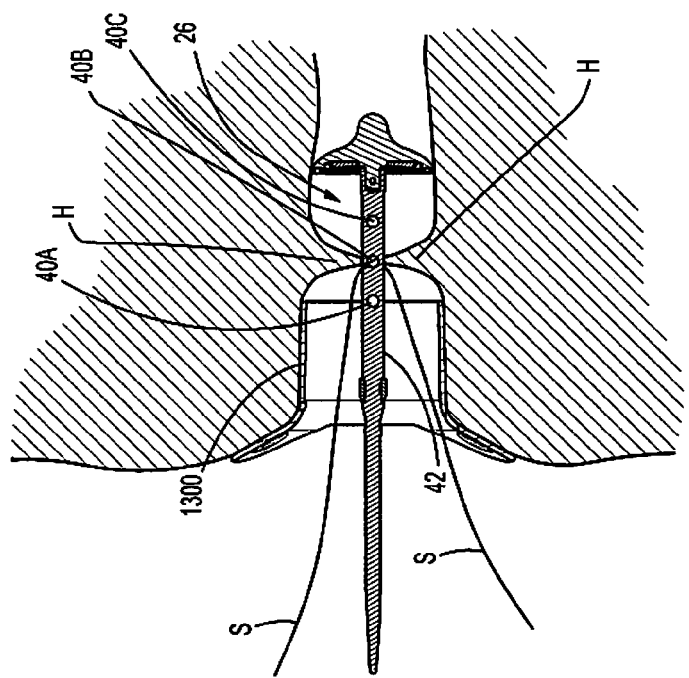
FIG. 13 is a longitudinal, cross-sectional view of the port component of the insertion device of FIG. 1 and the anvil assembly of the surgical fastener applying apparatus of FIG. 3 positioned within a patient following purse stringing and illustrating attachment of the suture to the anvil assembly of the apparatus.

FIGS. 1 and 2 illustrate one embodiment of the presently disclosed insertion device, which is identified by the reference character 1000. The insertion device 1000 is configured and dimensioned for use during a surgical procedure to enlarge an opening in a patient's tissue to facilitate access to an internal treatment site with a surgical instrument. During the following discussion, the insertion device 1000 will be discussed in the context of a surgical hemorrhoid procedure by way of example, wherein the target hemorrhoidal tissue "H" (see FIGS. 13, 14) is removed from a patient's anal canal using a surgical fastener applying apparatus.

Figure 4:
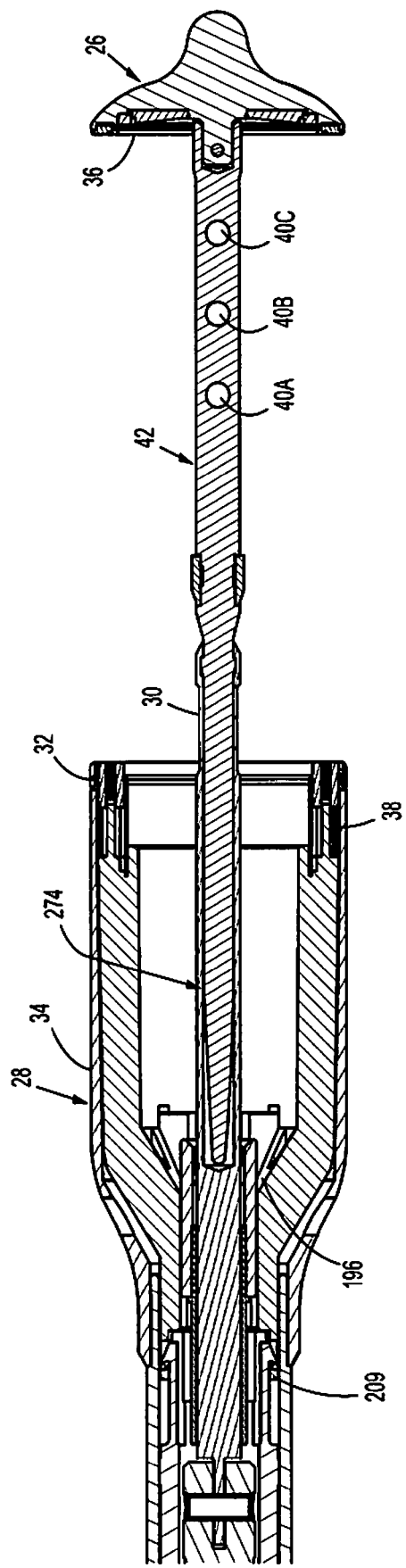
FIG. 4 is a partial, longitudinal, cross-sectional view of a portion of the surgical fastener applying apparatus illustrating anvil and shell assembly components thereof.

Referring to FIGS. 3 and 4, an exemplary embodiment of a suitable surgical fastener applying apparatus, which is identified by the reference character 10, will be described, and a brief overview of the structure and operation of the surgical fastener applying apparatus 10 will be provided. Additional details regarding the surgical fastener applying apparatus 10 can be obtained through reference to U.S. patent application Ser. No. 12/550,443 filed on Aug. 31, 2009, the entire contents of which are incorporated by reference herein. It should be understood however, that other surgical fastener applying apparatus can be used with the insertion devices disclosed herein.

The surgical fastener applying apparatus 10 includes a handle assembly 12, a central body portion 14 with an outer tube 16, and a distal head portion 18. The handle assembly 12 includes a stationary handle 20, a firing trigger 22, and a rotatable approximation knob 24.

The head portion 18 of the surgical fastener applying apparatus 10 includes an anvil assembly 26 and a shell assembly 28. The anvil assembly is repositionable between an unapproximated position, wherein the anvil assembly 26 is spaced a distance from the shell assembly 28 (as in FIG. 3), and an approximated position, wherein the anvil assembly 26 is closer to the shell assembly 28 to clamp tissue therebetween (see e.g. FIG. 15).

When the surgical fastener applying apparatus 10 is assembled, the anvil assembly 26 is positioned within an anvil retainer 30 that is movable relative to the shell assembly 28 via an operative connection to the approximation knob 24. Accordingly, during use of the surgical fastener applying apparatus 10, rotation of the approximation knob 24 effectuates movement of the anvil retainer 30, and consequently, the anvil assembly 26, in relation to the shell assembly 28 to thereby transition the anvil assembly 26 between the unapproximated and approximated positions.

The surgical fastener applying apparatus 10 further includes a firing mechanism to facilitate the ejection of a plurality of surgical fasteners 32 (FIG. 4) from the shell assembly 28 which are arranged in a circular array(s). The firing mechanism includes the aforementioned firing trigger 20 (FIG. 3), which is operatively connected to a pusher back 34 (FIG. 4) component of the shell assembly 28. Upon actuation (pivoting) of the firing trigger 20, distal movement thereof causes corresponding distal movement of the pusher back 34 via a pusher link to eject the surgical fasteners 32 from the shell assembly 28. Upon ejection from the shell assembly 28, the surgical fasteners 32 are forced into engagement with depressions (pockets) on an anvil plate 36 (FIG. 4) component of the anvil assembly 26 to thereby form the surgical fasteners 32. Contemporaneously with ejection of the surgical fasteners 32, a circular knife member 38 is advanced distally through the pusher back 34 into engagement with the anvil assembly 26 to thereby sever tissue positioned between the anvil assembly 26 and the shell assembly 28.

Referring back to FIGS. 1 and 2, the components and structure of the insertion device 1000 will be discussed in detail. The insertion device 1000 includes an obturator 1100 with a dilating tip 1102, an anoscope 1200, and a port 1300. In one embodiment of the insertion device 1000, it is envisioned that the anoscope 1200 and the port 1300 may be formed, either partially or wholly, from a clear material, e.g., polycarbonate, to facilitate the visualization of target tissue, as well as any adjacent or surrounding tissue, during the surgical procedure. However, alternative materials of construction, e.g., materials allowing less light to pass through the anoscope 1200 and the port 1300, are within the scope of the present disclosure.

The anoscope 1200 includes a dished proximal flange 1202, and a sleeve 1204 with respective proximal and distal ends 1206, 1208 that are spaced apart along a longitudinal axis "Y." The flange 1202 extends outwardly from the proximal end 1206 of the sleeve 1204 relative to the longitudinal axis "Y," and includes respective first and second circumferentially spaced ends 1210, 1212. The ends 1210, 1212 of the flange 1202 are connected by an arcuate portion 1214, and define a gap "G". The arcuate portion 1214 may define an arc of approximately 180°. However, the arc defined by the arcuate portion 1214 may be either larger or smaller in alternative embodiments of the present disclosure.

The anoscope 1200 further includes a single wing 1216 that extends outwardly from the flange 1202 relative to the longitudinal axis "Y" in a manner resulting in a configuration that is asymmetrical about a plane extending along the longitudinal axis "Y" that bisects the flange 1202. The wing 1216 is configured and dimensioned for manual engagement by the clinician to facilitate manipulation of the anoscope 1200 during the course of the surgical hemorrhoid procedure. In one embodiment of the anoscope 1200, the wing 1216 may be positioned adjacent one of the ends 1210, 1212 of the flange 1202, e.g., the second end 1212, as shown in FIG. 1. Alternatively, however, the wing 1216 may be positioned at a location between the ends 1210, 1212 of the flange 1202.

Figure 5:
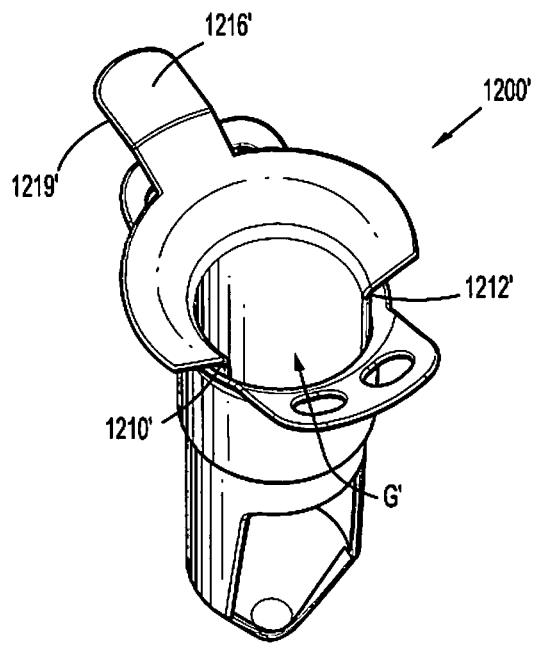
FIG. 5 is a top, perspective view of an alternative embodiment of the presently disclosed insertion device with the obturator removed.

Referring to FIG. 5, an embodiment of the anoscope, generally designated by reference numeral 1200', is illustrated wherein the wing 1216' is positioned at a location equidistant from the ends 1210', 1212' of the flange 1202' such that the wing 1216' is positioned opposite the gap "G'" defined between the ends 1210', 1212'. The arcuate portion may define an arc of approximately 180°, although smaller or greater arcs are also contemplated. In this embodiment, the configuration is symmetrical about a plane extending along the longitudinal axis "Y" that bisects the flange 1202', and the wing 1216' provides the clinician with a way to ascertain the position of the gap "G" to facilitate accurate placement of the anoscope relative to the target tissue H. The wing 1216' preferably angles upwardly similar to the wings of the embodiment of FIG. 17 and has a lip along a periphery to facilitate maneuverability. The anoscope of FIG. 5 is otherwise the same as the anoscope of FIG. 1 and can be used with the port and dilator of FIG. 1.

Referring again to FIGS. 1 and 2, the wing 1216 includes a proximal surface 1218 which may be substantially uniform in configuration, i.e., a proximal surface 1218 that is free from any indentations, protrusions, or other such irregularities. Alternatively, the proximal surface 1218 of the wing 1216 may include textured surfaces, or the like to facilitate manual manipulation of the anoscope 1200 by the clinician.

The sleeve 1204 of the anoscope 1200 extends distally from the flange 1202 and defines an internal dimension that allows for removable reception of the obturator 1100 therein. The sleeve 1204 includes a closed distal tip 1220 having an atraumatic, e.g., conical configuration. This configuration facilitates the dilation of tissue, such as the patient's anal canal, and thus, insertion and advancement of the anoscope 1200, as well as rotation of the anoscope 1200 once positioned internally.

Figure 6:
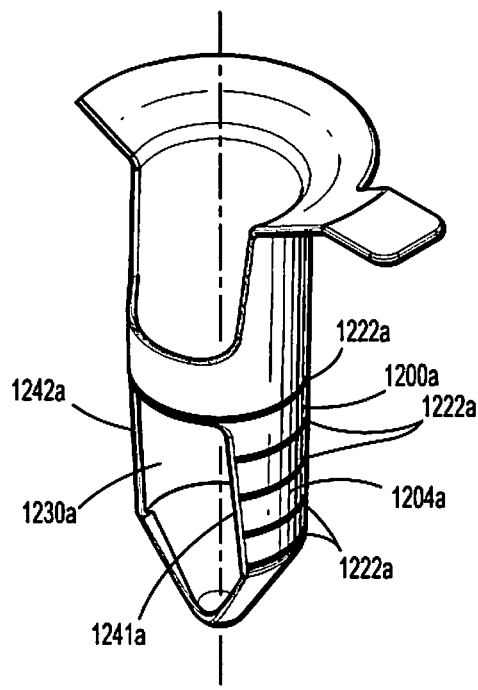
FIG. 6 is a top, perspective view of another embodiment of the presently disclosed insertion device with the obturator removed.

In one embodiment of the anoscope 1200*a*, which can be seen in FIG. 6, the sleeve 1204*a* may include markings 1222*a* to assist the clinician in the placement of purse strings. The markings are placed along an exterior of the body, adjacent distal opening 1230*a*. Preferably, the markings extend around the entire body from edge 1241*a* to edge 1242*a* of distal opening 1230*a*. Specifically, the markings 1222*a* allow the clinician to easily ascertain the depth to which the anoscope 1200*a* has been inserted within the opening in the patient's tissue, e.g., the depth within the patient's anal canal. By allowing the clinician to easily determine the depth to which the anoscope 1200*a* has been inserted, the markings 1222*a* facilitate the placement of purse strings at a consistent distance from the opening in the patient's tissue. Although five markings 1220 are shown, a different number of markings is also contemplated. In all other respects, anoscope 1200*a* is the same as anoscope 1200 of FIG. 1 and can be utilized with the port and dilator of FIG. 1.

Returning to FIGS. 1 and 2, the sleeve 1204 also includes an open region 1224 that extends longitudinally therethrough along the axis "Y," and a bridge 1226 that spans the open region 1224 to thereby divide the open region 1224 into respective proximal and distal openings 1228, 1230. The bridge 1226 may extend across the open region 1224 to define an arc having any suitable dimensions. For example, as illustrated in FIG. 1, the arc defined by the bridge 1226 may extend less than 180°. However, an arc greater than 180° is also within the scope of the present disclosure.

The configuration of the bridge 1226 may be altered or varied in alternative embodiments of the anoscope 1200 to realize any suitable axial length. In one particular embodiment, the bridge 1226 defines an axial length of about 1.5 cm (approximately 0.59 inches), and is positioned such that respective proximal and distal ends 1232, 1234 of the bridge 1226 are located about 3 cm (approximately 1.18 inches) and about 4.5 cm (approximately 1.77 inches) from the proximal end 1206 of the sleeve 1204, i.e., from the point of contact between the flange 1202 and the sleeve 1204. In this embodiment, during the course of a hemorrhoid procedure, upon insertion of the anoscope 1200 into the patient's anal canal, the distal opening 1230 in the sleeve 1204 will be positioned above (proximally) of the dentate line, which is located in the human anal canal about 2 cm (approximately 0.78 inches) from the anus. With the distal opening 1230 positioned proximally of the dentate line, purse stringing, and subsequent tissue removal, will also occur proximally of the dentate line.

Figure 7:
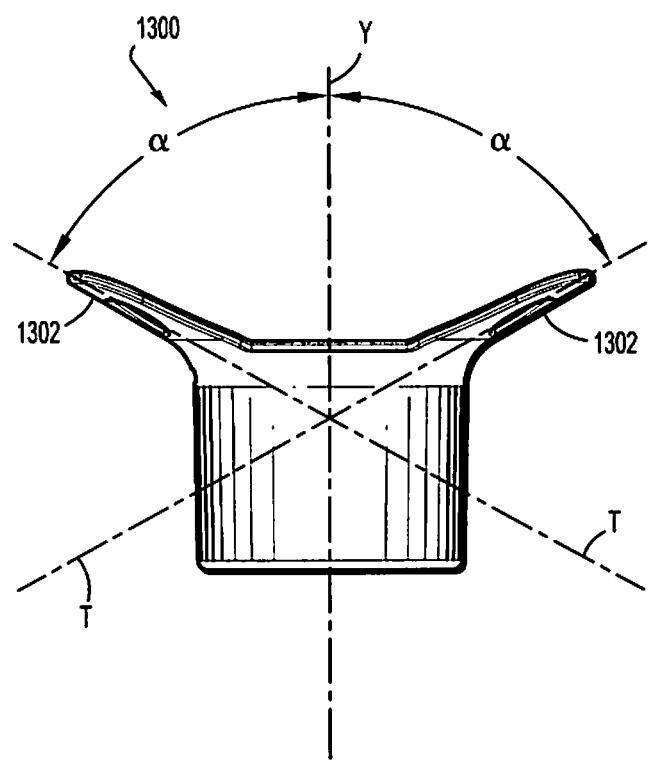
FIG. 7 is a side, plan view of the port component of the insertion device of FIG. 1.

With reference now to FIGS. 1 and 7, the port 1300 of the insertion device 1000 will be discussed. The port 1300 defines an internal dimension that allows for removable reception of the anoscope 1200, and includes a pair of wings 1302 that are configured and dimensioned for manual engagement by the clinician to facilitate handling and manipulation of the port 1300 during the course of the surgical procedure. The wings 1302 extend outwardly from the port 1300 relative to the longitudinal axis "Y." Specifically, the wings 1302 each extend along an axis "T" (FIG. 7) that is transverse in relation to the longitudinal axis "Y" to subtend an angle α therewith. It is envisioned that the angle α may lie substantially within the range of approximately 45° to approximately 90°. For example, in the embodiment of the port 1300 illustrated in FIGS. 1 and 7, the axis "T" along which the wings 1302 extends defines an angle of approximately 55° with the longitudinal axis "Y." However, larger and smaller values for the angle α are also contemplated.

As best seen in FIG. 1, the wings 1302 of the port 1300 include a pair of apertures 1304 that are configured and dimensioned to receive a flexible member (not shown), such as a suture, that can be secured to the patient's tissue in order to facilitate fixation of the port 1300 relative thereto. However, an embodiment of the port 1300 in which the wings 1302 have a different number of apertures or are devoid of the apertures is also contemplated.

Figure 8:
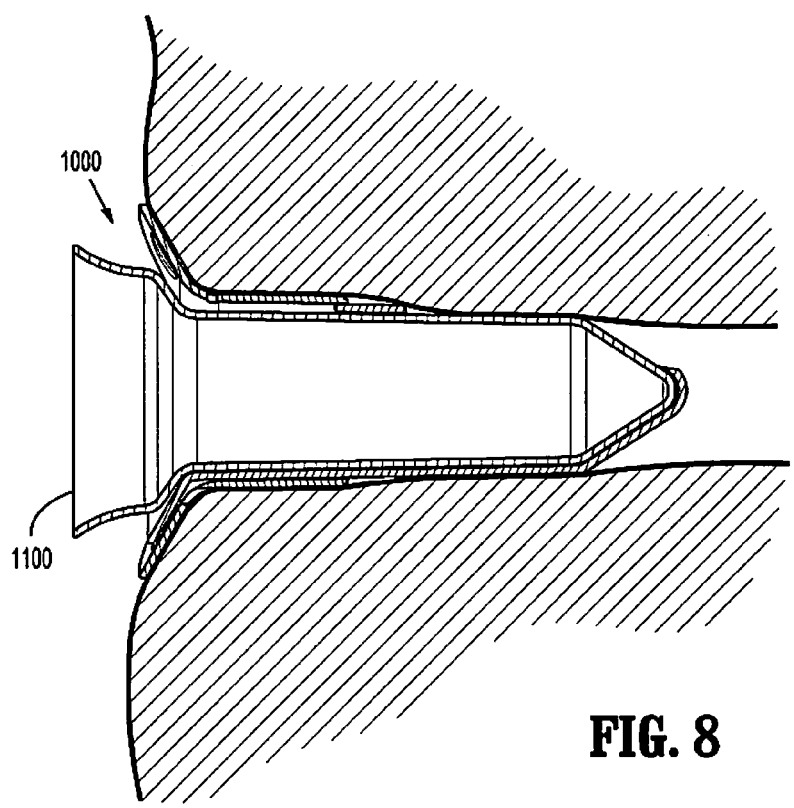
FIG. 8 is a longitudinal, cross-sectional view of the insertion device of FIG. 1 shown assembled and positioned within a patient.
Figure 9:
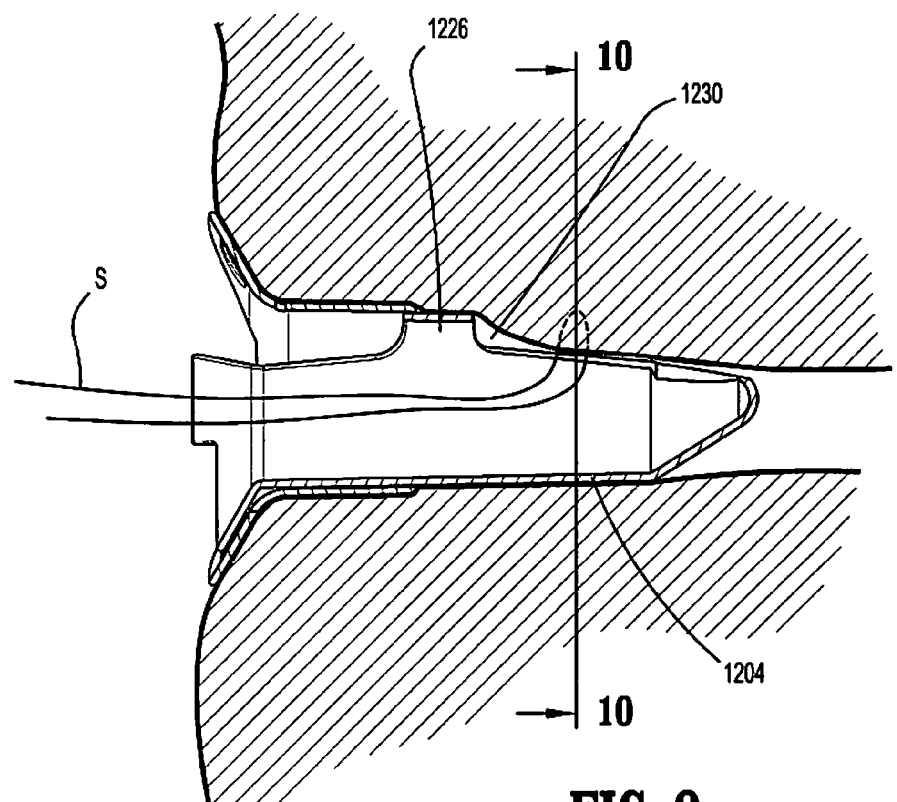
FIG. 9 is a longitudinal, cross-sectional view of the insertion device of FIG. 1 positioned within a patient following removal of the obturator.

The use and operation of the insertion device 1000 (FIGS. 1, 2) will be discussed in connection with the surgical fastener applying apparatus 10 (FIGS. 3, 4) in the context of a surgical hemorrhoid procedure, it being understood that the other insertion devices (i.e. other anoscopes) disclosed herein would be used in a similar manner. Prior to insertion, the anvil assembly 26 is removed from the anvil retainer 30, and the insertion device 1000 is assembled as illustrated in FIG. 2. Specifically, the anoscope 1200 is positioned coaxially within the port 1300, and the obturator 1100 is positioned coaxially within the sleeve 1204 of the anoscope 1200. The assembled insertion device 1000 is then inserted transanally into an opening in the patient's tissue such that the bridge 1226 is positioned above the dentate line (see FIG. 8). Thereafter, the obturator 1100 is removed, leaving the anoscope 1200 positioned within port 1300, as seen in FIG. 9, such that the port 1300 extends from the patient's anus. Either prior or subsequent to assembly of the insertion device 1000, the port 1300 may be optionally fixed to the patient's tissue by the aforementioned flexible member (not shown).

Figure 10:
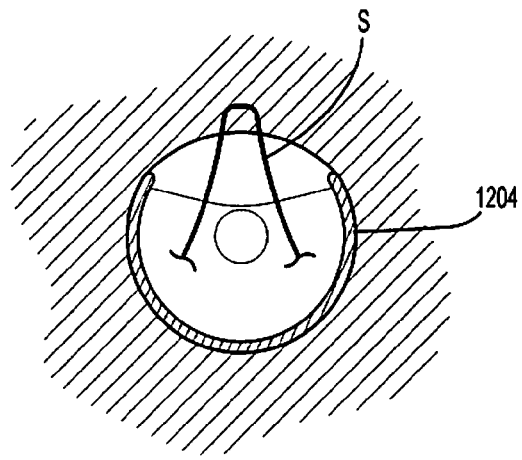
FIGS. 10-12 are proximal, end views of the insertion device positioned within a patient following removal of the obturator illustrating a purse stringing procedure in which a suture is attached to target tissue.
Figure 11:
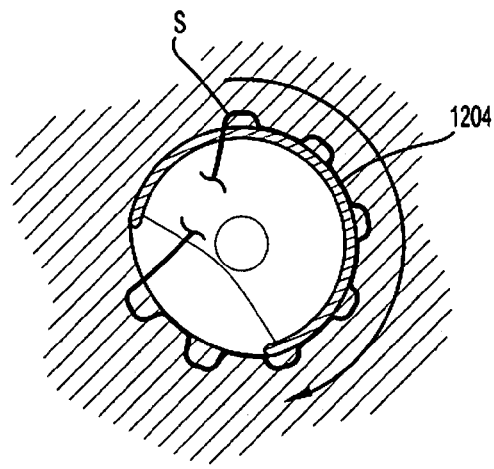
Figure 12:
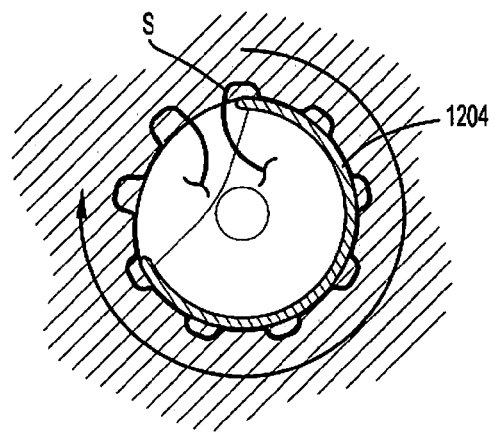

As seen in FIG. 9, following removal of the obturator 1100, the target tissue, e.g., internal hemorrhoidal tissue "H," is received by the distal opening 1230 in the sleeve 1204 such that the tissue "H" is positioned within the sleeve 1204 of the anoscope 1200. The clinician then attaches a length of suture to the target tissue "H," a procedure which is generally referred to as "purse stringing." Thereafter, the anoscope 1200 can be rotated within the port 1300 to one or more subsequent positions, exemplified in the transition between FIGS. 10, 11, and 12, such that additional internal hemorrhoidal tissue "H," if any, can be received within the distal opening 1230, and purse stringed.

After purse stringing is completed, the anoscope 1200 is removed from the patient's anus. The anvil assembly 26 (FIG. 13) of the surgical fastener applying apparatus 10 is then inserted through the port 1300 into the patient's anal cavity, and the two ends of the suture "S" are attached to the anvil assembly 26. For instance, in the illustrated embodiment of the surgical fastener applying apparatus 10, the ends of the suture "S" are inserted into aperture 40B of the apertures 40A-40C (FIGS. 3, 4, 13) formed in a center rod 42 component of the anvil assembly 26. The apertures 40A-40C through which the ends of the suture "S" are inserted is dependent upon the amount of tissue the clinician wishes to draw into the shell assembly 28 during approximation of the anvil assembly 26 and the shell assembly 28, the proximal-most aperture 40A providing the greatest amount of tissue. The length of the suture "S" is such that the suture "S" extends from the port 1300 after positioning within the select aperture 40A-40C.

Figure 14:
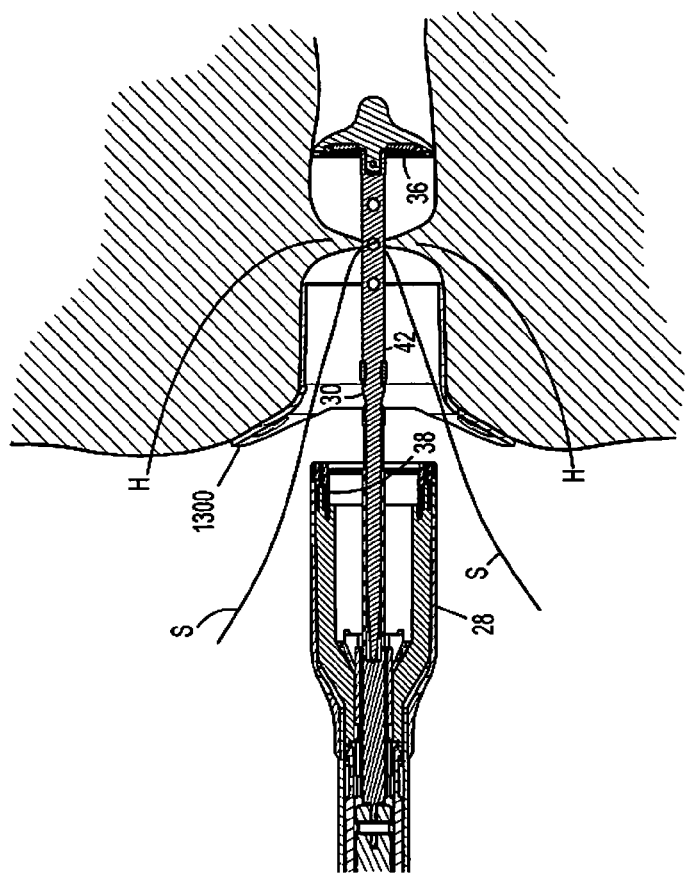
FIG. 14 is a partial, longitudinal, cross-sectional view of the port component of the insertion device of FIG. 1 and the anvil assembly of the surgical fastener applying apparatus of FIG. 3 positioned within a patient following purse stringing and attachment of the anvil assembly to an anvil retainer of the surgical apparatus.
Figure 16:
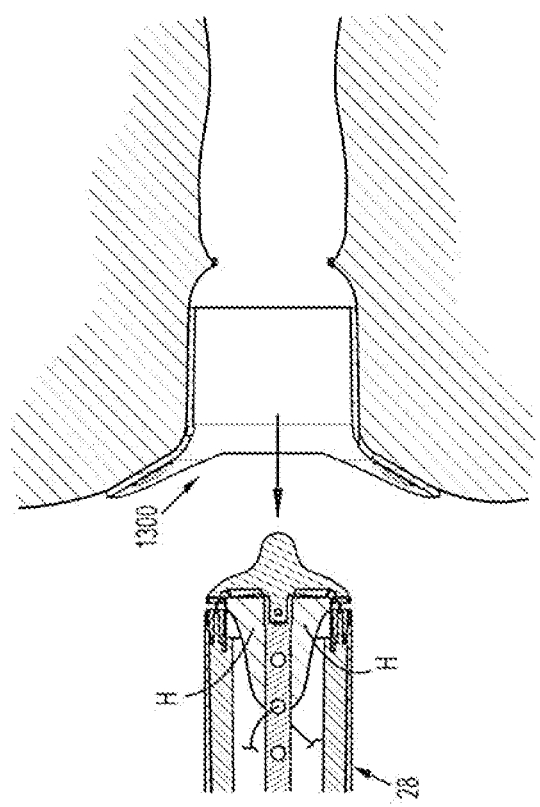
FIG. 16 is a partial, longitudinal, cross-sectional view of the distal end of the surgical fastener applying apparatus of FIG. 3 following removal from the port component of the insertion device of FIG. 1 from the patient illustrating the removed target tissue within the shell assembly of the apparatus.
Figure 15:
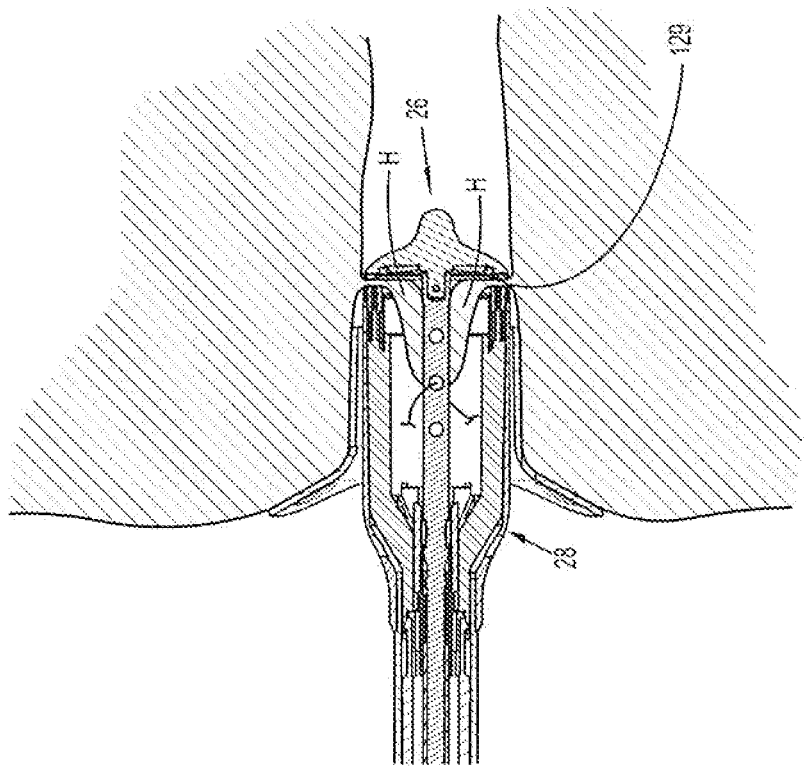
FIG. 15 is a partial, longitudinal, cross-sectional view illustrating a distal end of the surgical fastener applying apparatus of FIG. 3 positioned within the port component of the insertion device of FIG. 1 following approximation of the anvil assembly and the shell assembly of the apparatus.

Following attachment of the suture "S" to the center rod 42, the anvil assembly 26 is re-connected to the surgical fastener applying apparatus 10 by positioning the anvil assembly 26 within the anvil retainer 30, as shown in FIG. 14. Next, the approximation knob 24 (FIG. 3) of apparatus 10 is rotated to move the anvil assembly 26 proximally towards the shell assembly 28 such that the target tissue "H" is drawn into, and positioned within, the shell assembly 28, as shown in FIG. 15. The surgical fastener applying apparatus 10 is then fired to sever and fasten the target tissue "H." After severing of the tissue "H," the surgical fastener applying apparatus 10 can be removed from the port 1300 with the tissue "H" positioned within the shell assembly 28, as shown in FIG. 16.

Figure 17:
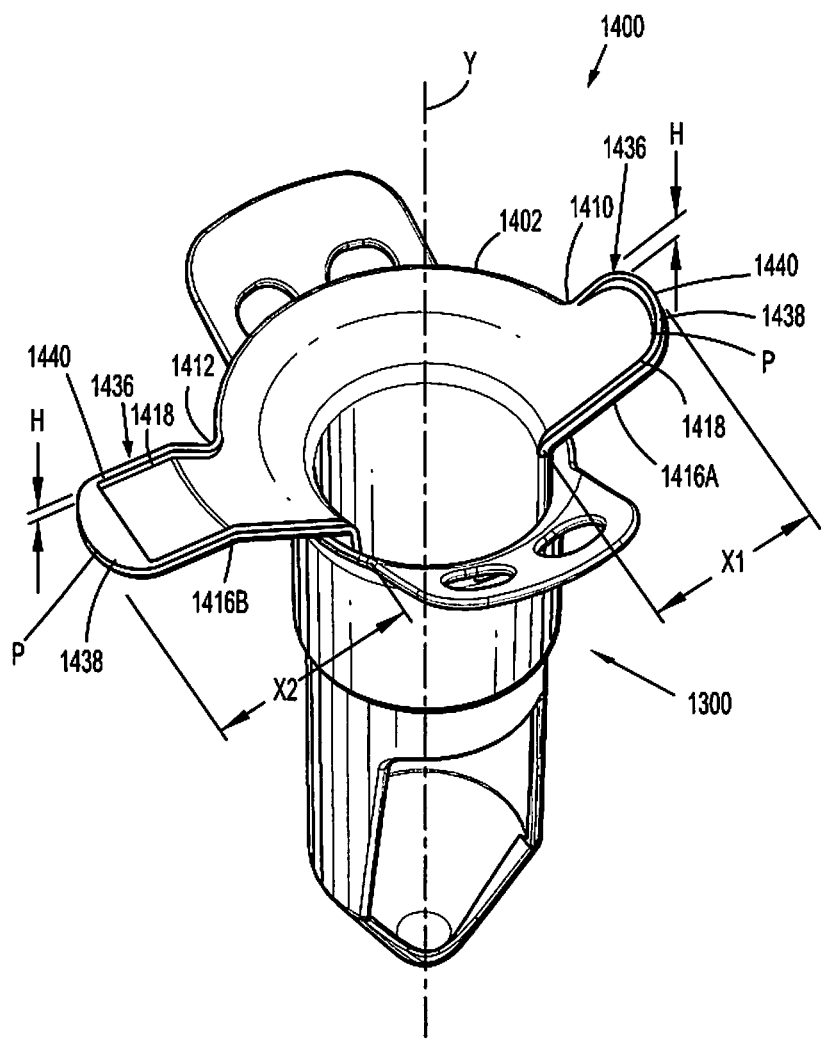
FIG. 17 is a top, perspective view of another embodiment of the presently disclosed insertion device with the obturator removed.
Figure 18:
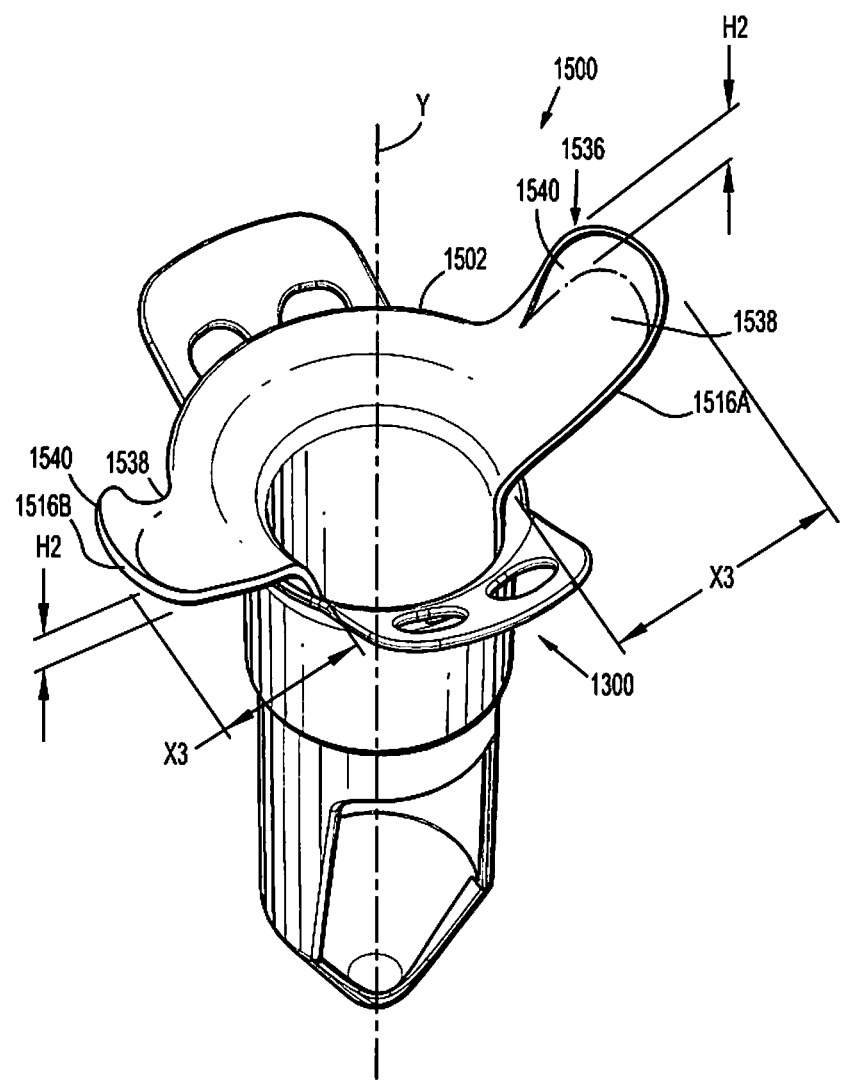
FIG. 18 is a top, perspective view of still another embodiment of the presently disclosed insertion device with the obturator removed.

With reference now to FIGS. 17 and 18, alternative embodiments of the anoscope component of the presently disclosed insertion device 1000 (FIG. 1) will be discussed. Each embodiment of the anoscope discussed herein below is similar to the anoscope 1200 that was discussed above with respect to FIGS. 1 and 2, for example, and accordingly, will only be described with respect to any differences therefrom.

FIG. 17 illustrates an embodiment of the anoscope that is identified by the reference character 1400 and is shown positioned within the port 1300. In contrast to the aforedescribed anoscope 1200 (FIGS. 1, 2), which includes only a single wing 1216, the anoscope 1400 includes a first wing 1416A and a second wing 1416B that each extend outwardly from the dished flange 1402. In the illustrated embodiment, the wings 1416A, 1416B are positioned adjacent the ends 1410, 1412 of the flange 1402, respectively. More specifically, in the illustrated embodiment, the ends 1410, 1412 of the flange 1402, and thus, the wings 1416A, 1416B, are diametrically opposed. In alternative embodiments of the anoscope 1400, however, it is envisioned that the wings 1416A, 1416B may be spaced from the ends 1410, 1412 of the flange 1402.

The structure of the first wing 1416A differs from that of the second wing 1416B such that the configuration of the anoscope 1400 is asymmetrical about a plane extending along the longitudinal axis "Y" that bisects the flange 1402. In the specific embodiment of the anoscope 1400 illustrated in FIG. 17, the first wing 1416A extends outwardly from the flange 1402 a first distance "X1," whereas the second wing 1416B extends outwardly from the flange 1402 a second, greater distance "X2." The shorter distance "X1" defined by the first wing 1416A reduces the likelihood that the first wing 1416A will interfere with manipulation of the anoscope 1400 during the surgical procedure via contact with the patient's tissue.

To facilitate manual engagement with the wings 1416A, 1416B, the wings 1416A, 1416B include a raised protrusion 1436. The protrusions 1436 extend away from the wings 1416A, 1416B in a proximal direction to define a height "H," and corresponding adjacent area 1438 to thereby enhance maneuverability of the anoscope 1400.

In the illustrated embodiment, the protrusions 1436 are configured as ribs, or flanges, 1440 that are positioned adjacent a peripheral edge "P" of the wings 1416A, 1416B. It should be understood, however, that in alternative embodiments of the anoscope 1400, the protrusion 1436 may assume any configuration suitable for the intended purpose of increasing the clinician's control over, and ability to manipulate, the anoscope 1400, and that other configurations for the protrusion 1436 are not beyond the scope of the present disclosure. It is also envisioned that the wings 1416A, 1416B may be devoid of the protrusions 1436 such that the wings 1416A, 1416B include a substantially uniform proximal surface 1418, i.e., a surface that is free from any indentations, protrusions, or other such irregularities, as discussed above with respect to the anoscope 1200 (FIGS. 1, 2).

FIG. 18 illustrates another embodiment of the anoscope that is identified by the reference character 1500 and is shown positioned within the port 1300. Like the anoscope 1400 described with respect to FIG. 17, the anoscope 1500 includes a first wing 1516A and a second wing 1516B that each extend outwardly from the dished flange 1502. However, in contrast to the first and second wings 1416A, 1416B of the anoscope 1400, the structure of the first wing 1516A is identical to that of the second wing 1516B such that the configuration of the anoscope 1500 is symmetrical about a plane extending along the longitudinal axis "Y" that bisects the flange 1502. In the specific embodiment of the anoscope 1500 illustrated in FIG. 18, the first wing 1516A and the second wing 1516B each extend outwardly from the flange 1502 a distance "X3." The wings 1516A and 1516B curve proximally forming arcuate regions.

To facilitate manual engagement with the wings 1516A, 1516B, as with the aforedescribed anoscope 1400 (FIG. 17), it is envisioned that the wings 1516A, 1516B may each include a raised protrusion 1536. The protrusions 1536 extend away from the wings 1516A, 1516B in the proximal direction to define a height "H2" that is greater than the height "H" defined by the protrusions 1436 included on the wings 1416A, 1416B of the anoscope 1400 (FIG. 17). The increased height "H2" of the protrusions 1536 increases both the depth of the surfaces 1538 defined thereby, as well as the surface area available for contact with the clinician, e.g., with the clinician's finger(s). Thus, the increased height "H2" of the protrusions 1536 further increases the clinician's control over, and ability to manipulate, the anoscope 1500.

Although illustrated as a rib, or flange, 1540 that extends along the peripheral edge "P" of the wings 1516A, 1516B, it should be understood that the protrusions 1536 may assume alternative configurations in additional embodiments of the anoscope 1500, and that the protrusions 1536 (as well as protrusions 1436 of FIG. 17) may be spaced from the peripheral edge "P" of the wings without departing from the scope of the present disclosure.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the invention based on the above-described embodiments. Accordingly, the invention is not to be limited by what has been particularly shown and described, except as indicated by the appended claims.

What is claimed is:

1. An insertion device for use during a surgical procedure to enlarge an opening in a patient's tissue to facilitate access to an internal treatment site with a surgical instrument, the insertion device comprising an anoscope including a flange, and an elongate body having an outer wall, and proximal and distal ends extending distally from the flange, wherein the flange includes first and second circumferentially spaced ends defining a gap therebetween, and at least one wing extending outwardly from the flange, the at least one wing being spaced a first distance from the first end of the flange, and a second, different distance from the second end of the flange such that the anoscope includes a configuration that is asymmetrical about a first vertical plane coincident with a central longitudinal axis of the insertion device bisecting the flange to define two equal halves, the anoscope further defining a second vertical plane coincident with the central longitudinal axis and perpendicular in relation to the first vertical plane, the outer wall of the body including a first opening spaced longitudinally from a second opening, the first and second openings being located entirely on a common side of the second vertical plane and separated by a portion of the outer wall, and extending through the outer wall of the body, the first opening being in direct communication with the gap defined between the first and second ends of the flange, the second opening being positioned and configured to receive tissue when the anoscope is disposed within the anus of a patient.

2. The insertion device of claim 1, wherein the at least one wing includes a protrusion extending in a proximal direction.

3. The insertion device of claim 1, wherein the gap defined between the first and second ends of the flange is configured and dimensioned to receive tissue.

4. The insertion device of claim 3, wherein the at least one wing consists of a single wing.

5. The insertion device of claim 4, wherein the wing is positioned at one of the ends of the flange.

6. The insertion device of claim 1, wherein the first and second openings are aligned along the central longitudinal axis.

7. The insertion device of claim 1, further including a dilator configured and dimensioned for positioning within the body of the anoscope.

8. The insertion device of claim 1, further including a port defining a longitudinal opening therethrough configured and dimensioned to receive the anoscope, the port being configured and dimensioned for positioning within the opening in the tissue.

9. An insertion device for use during a surgical procedure to enlarge an opening in a patient's tissue to facilitate access to an internal treatment site with a surgical instrument, the insertion device comprising an anoscope including a flange, and an elongate body having an outer wall extending distally from the flange, wherein the flange includes first and second circumferentially spaced ends defining a gap therebetween, and at least one wing extending outwardly from the flange, the at least one wing being spaced a first distance from the first end of the flange, and a second, different distance from the second end of the flange such that the anoscope includes a configuration that is asymmetrical with respect to a first vertical plane coincident with a central longitudinal axis of the insertion device that divides the flange into two equal portions, the anoscope further defining a second vertical plane coincident with the central longitudinal axis and perpendicular in relation to the first vertical plane, the outer wall of the body including first and second discrete openings extending therethrough, the first and second openings being located entirely on a common side of the second vertical plane, the first opening being in direct communication with the gap defined between the first and second ends of the flange, the second opening being positioned and configured to receive tissue to be manipulated when the anoscope is positioned within the anus of a patient.

10. The insertion device of claim 9, wherein the first and second openings are aligned along the central longitudinal axis.

11. The insertion device of claim 10, wherein the first opening is spaced longitudinally from the second opening.

12. The insertion device of claim 11, wherein the first and second openings are separated by a portion of the outer wall.

13. The insertion device of claim 9, wherein the at least one wing includes a protrusion extending in a proximal direction.

14. The insertion device of claim 9, wherein the gap defined between the first and second ends of the flange is configured and dimensioned to receive tissue.

15. The insertion device of claim 14, wherein the at least one wing consists of a single wing.

16. The insertion device of claim 15, wherein the wing is positioned at one of the ends of the flange.

17. The insertion device of claim 9, further including a dilator configured and dimensioned for positioning within the body of the anoscope.

18. The insertion device of claim 9, further including a port defining a longitudinal opening therethrough configured and dimensioned to receive the anoscope, the port being configured and dimensioned for positioning within the opening in the tissue.

19. The insertion device of claim 1, wherein the second opening extends proximally from the distal end of the elongate body.

20. The insertion device of claim 9, wherein the second opening extends proximally from the distal end of the elongate body.

21. An insertion device for enlarging an opening in tissue to permit a surgical instrument to access an internal treatment site, the insertion device comprising:
 a flange including first and second circumferentially spaced ends, the first and second ends defining a gap therebetween;
 a wing extending outwardly from the flange, the wing being spaced a first distance from the first end of the flange and a second distance from the second end of the flange, the second distance being different from the first distance;
 an elongate body having an outer wall defining first and second openings spaced longitudinally from one another, longitudinally from one another, the first opening in direct communication with the gap, a vertical plane being defined through the body, the vertical plane being coincident with the longitudinal axis of the elongate body and bisecting the flange, the first and second openings being positioned entirely on one side of the vertical plane in longitudinal alignment with one another, the second opening being positioned and configured to receive tissue to be sutured during a surgical procedure.

22. The insertion device of claim 21, wherein the elongate body includes a conical distal end portion, the first opening being positioned adjacent a proximal end of the elongated body and the second opening extending into the conical distal end portion of the elongate body.

* * * * *